US012636407B1

(12) United States Patent
Burckhardt et al.

(10) Patent No.: US 12,636,407 B1
(45) Date of Patent: May 26, 2026

(54) SOLUBLE PLACENTAL ECM

(71) Applicant: REGENTX PARTNERS, LLC, San Antonio, TX (US)

(72) Inventors: Oliver Burckhardt, Philadelphia, PA (US); Laura Del Carmen Bordallo Castillo, San Antonio, TX (US); James Poser, San Antonio, TX (US)

(73) Assignee: RegenTX Partners, LLC, San Antonio, TX (US)

( * ) Notice: Subject to any disclaimer, the term of this patent is extended or adjusted under 35 U.S.C. 154(b) by 585 days.

(21) Appl. No.: 17/946,030

(22) Filed: Sep. 15, 2022

Related U.S. Application Data

(60) Provisional application No. 63/244,418, filed on Sep. 15, 2021, provisional application No. 63/244,443, filed on Sep. 15, 2021.

(51) Int. Cl.
| | |
|---|---|
| *A61L 27/36* | (2006.01) |
| *A61K 9/08* | (2006.01) |
| *A61K 35/50* | (2015.01) |
| *A61K 38/39* | (2006.01) |

(52) U.S. Cl.
CPC ............ *A61L 27/3633* (2013.01); *A61K 9/08* (2013.01); *A61K 35/50* (2013.01); *A61K 38/39* (2013.01)

(58) Field of Classification Search
None
See application file for complete search history.

(56) References Cited

U.S. PATENT DOCUMENTS

2008/0181967 A1* 7/2008 Liu ......................... A61P 41/00
424/583
2016/0263280 A1* 9/2016 Harrell ................ A61L 27/3604

OTHER PUBLICATIONS

Yang et al., Effect of Cardioplegic and Organ Preservation Solutions and Their Components on Coronary Endothelium-Derived Relaxing Factors, 2005, The Society of Thoracic Surgeons, vol. 80, p. 1-13 (Year: 2005).*
Sweeney et al., Perioperative Intravenous Fluid Therapy for Adults, 2013, Ulster Med, vol. 82, p. 171-178 (Year: 2013).*
Badylak, Stephen F., Donald O. Freytes, and Thomas W. Gilbert. "Extracellular matrix as a biological scaffold material: Structure and function." Acta biomaterialia 5.1 (2009): 1-13.
Frantz, Christian, Kathleen M. Stewart, and Valerie M. Weaver. "The extracellular matrix at a glance." Journal of cell science 123.24 (2010): 4195-4200.
Chen, C. P., and John D. Aplin. "Placental extracellular matrix: gene expression, deposition by placental fibroblasts and the effect of oxygen." Placenta 24.4 (2003): 316-325.

(Continued)

*Primary Examiner* — Tracy Vivlemore
*Assistant Examiner* — Hanna Marie Thueson
(74) *Attorney, Agent, or Firm* — Blank Rome LLP

(57) ABSTRACT
The invention is directed to a composition of soluble placental ECM in storage solution and the methods of manufacture related thereto. The solubilized placental ECM solution is manufactured through a process of partitioning placental ECM from the placental tissue in a high acidic pH environment and performing an ultrafiltration step and diafiltration step through a tangential flow filtration system to increase the pH. The soluble placental ECM retains the native characteristics of placental ECM components and includes collagens (types I, III, V, VI, IX, and X), elastin, laminin, and fibronectin.

24 Claims, 6 Drawing Sheets

1

| | |
|---|---|
| Placental Tissue Acquisition | 10 |
| Gross Tissue Processing | 20 |
| Cleaning and Decellularization | 30 |
| Partitioning | 40 |
| Pre-Filtration | 50 |
| Ultrafiltration | 60 |
| Diafiltration | 70 |
| Sterilization | 80 |
| Package | 90 |

(56)          References Cited

OTHER PUBLICATIONS

Burk, Janina, et al. "Freeze-thaw cycles enhance decellularization of large tendons." Tissue Engineering Part C: Methods 20.4 (2014): 276-284.
Bosman, Fred T., and Ivan Stamenkovic. "Functional structure and composition of the extracellular matrix." The Journal of Pathology: A Journal of the Pathological Society of Great Britain and Ireland 200.4 (2003): 423-428.
Hoshiba, Takashi, and Tetsuji Yamaoka. "Extracellular matrix scaffolds for tissue engineering and biological research." (2019).
Barker, G., et al. "Placental water content and distribution." Placenta 15.1 (1994): 47-56.

* cited by examiner

SOLUBLE PLACENTAL ECM

CROSS-REFERENCES TO RELATED APPLICATIONS

This application claims the benefit of U.S. Provisional Application Ser. No. 63/244,418, filed Sep. 15, 2021 entitled Soluble Placental Extracellular Matrix and 63/244,443, filed Sep. 15, 2021 entitled Soluble Placental Extracellular Matrix, which are both incorporated by reference herein.

STATEMENT REGARDING FEDERALLY SPONSORED RESEARCH OR DEVELOPMENT

Not applicable.

BACKGROUND OF THE INVENTION

1. Field of the Invention

The present invention relates to a composition of soluble placental extracellular matrix ("ECM") allograft used for wound care.

2. Background of the Related Art

The placenta is a complex organ necessary for fetal development in mammals as it facilitates nutrient and waste exchange among other important functions. Like the fetus, the placenta increases in size and complexity over the course of the pregnancy. At birth, the average placenta weighs over a pound and is comprised of several layers including the amnion, chorion, intervillous space, and decidua.

The extracellular matrix (ECM) of placental tissue contains fibrous and adhesive glycoproteins that naturally assemble into a three-dimensional structure that, among other functions, supports, cushions, and connects the cells and microenvironment of the placental tissues. The placental ECM provides pathways for cell migration as well as storage and migration of nutrients, growth factors, and other physiological components. Mammalian ECM is known to reorganize and undergo increased expression due to physiological factors. The placental ECM comprises various macromolecules, including collagens (type I, III, V, VI, IX, and X), elastin, laminin, fibronectin, and proteoglycans.

Collagen is the most abundant fibrous protein within the interstitial placental ECM and is the main structural element in placental ECM. It provides tensile strength, regulates cell adhesion, supports chemotaxis and cell migration, and directs tissue development. The structural role of collagen includes its interaction with the cellular and other structural elements of the tissue.

Elastin naturally associates with collagen in the ECM. Elastin fibers provide recoil (i.e., functional elasticity) to tissues that undergo repeated stretch. Elastin stretch is crucially limited by tight association with collagen fibrils, thereby physically and functionally connecting the ECM elements.

Laminins are structural proteins in the ECM that actively influence cell differentiation, migration, and adhesion.

Fibronectin is intimately involved in directing the organization of the ECM and has a crucial role in mediating cell attachment and function. Fibronectin can unfold and be stretched several times its original length, serving as a mechano-regulator and conduit for cellular migration.

Proteoglycans (PGs), which are ECM proteins that are attached to one or more glycosaminoglycan chains, retain several times their weight in water forming a type of hydrated gel that fills extracellular interstitial space within the placental ECM. PGs have a wide variety of functions that reflect their unique hydration, cell adherence, lubricity and force-resistance (i.e., cushioning) properties. In the placenta, the PGs in association with collagen fibers generate a molecular structure within the ECM that is essential for mechanical buffering (i.e., ductility/flexibility) and tissue hydration.

Many mammalian organs, including skin, rely on ECM to perform the functions of the organ and for repair. For example, the ECM of skin is important to facilitate wound healing as the ECM promotes cell migration, migration and storage of nutrients, cytokines, growth factors, and other physiological components. Application of ECM and ECM components to a wound is known to support, promote, and accelerate wound healing.

It is desired to develop a minimally manipulated placental ECM allograft for use in wound care applications whether the wound is from disease, surgery, or accident. It is further desired to develop an efficient manufacturing process that preserves the native placental ECM macromolecules. A majority of most allografts for this purpose are thin sheets of tissue that are difficult to use, tear easily, and are limited in size as compared to wound size. It is desirable to develop a soluble placental ECM allograft to aid in application for wound care.

SUMMARY OF THE INVENTION

The present invention is manufactured through a plurality of steps intended to utilize non-aggressive techniques with minimal tissue manipulation to result in a product that maintains native placental ECM. The process includes the steps of gross processing the tissue to remove blood vessels, clots, and other undesired portions of the placenta. The placental tissue is then cleaned and decellularized. Next, the placental tissue is partitioned, or separated, through soaking in a weak organic acid solution. The partitioning step solubilizes the placental ECM into the weak organic acid solution. The solubilized placental ECM solution is ultrafiltered. The solubilized placental ECM solution is then diafiltered with an exchange solution to remove the weak organic acid and reduce the acidity level. The solubilized placental ECM solution is then sterilized and packaged in a storage solution. where it may be applied directly to a wound. The manufacturing process does not alter the characteristics of native placental ECM and several key proteins are retained including collagens (types I, III, V, VI, IX, and X), elastin, laminin, and fibronectin.

DETAILED DESCRIPTION OF THE INVENTION

Figure 1:
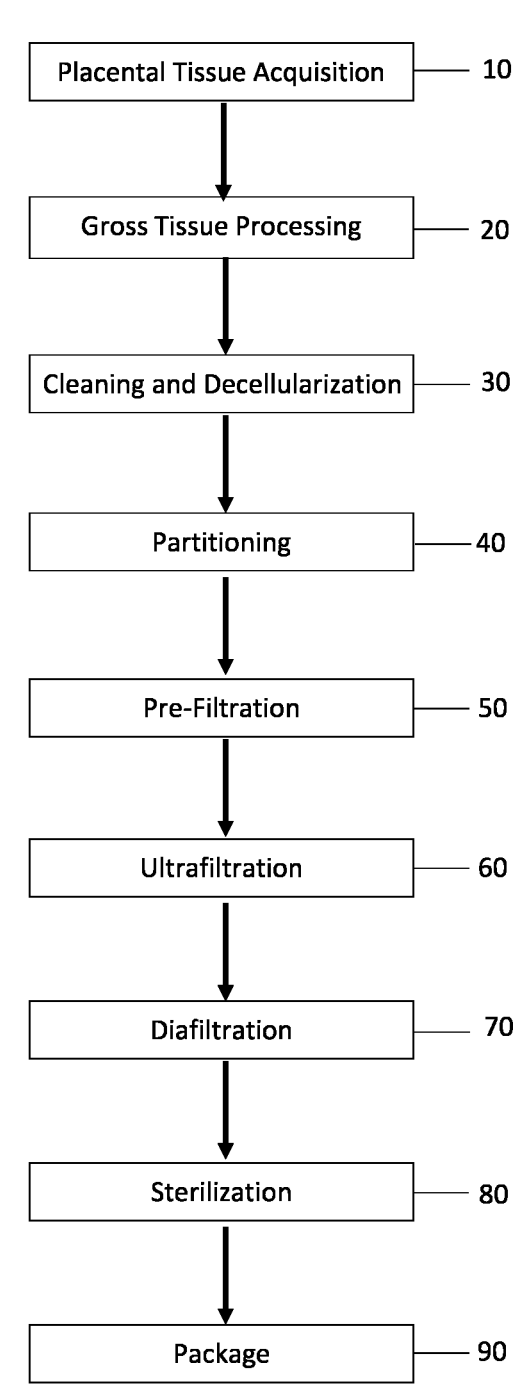
FIG. 1 is an overview flowchart of the manufacturing process for soluble placental ECM for one embodiment.

FIG. 1 depicts an overview of the manufacturing process 1. The general steps, as are discussed in more detail herein, include tissue acquisition 10, gross tissue processing 20, cleaning and decellularization 30, partitioning 40, pre-filtration 50, ultra-filtration 60, diafiltration 70, sterilization 80, and packaging 90. The invention is described in terms of a human placenta but other mammalian placenta may be used as the starting tissue. The whole placenta tissue is acquired 10 through generally accepted means and patient consent. In one embodiment, the placental tissue is frozen until donor eligibility is determined to include screening for disease and meets acceptance standards. Frozen placental tissue is preferred as the freezing process kills live cells but non-frozen placenta may also be used. Information pertaining to the donor shall be notated and at all times. Current Good Manufacturing Practices shall be performed in manufacturing with the present invention including notating records related to each step.

Once the placental tissue is approved for use, the placental tissue undergoes gross tissue processing 20. The placental tissue is first thawed. In one embodiment, the amnion membrane, including the spongy layer, is removed from the placenta. The chorion plate along with large vessels are cut from the placenta. Blood clots and blood components are removed and discarded. The remaining tissue is placed into an empty sterile canister. The tissue is submerged in 0.9% sterile saline and rinsed, at least one time, for at least five minutes. Multiple rinses may be utilized. During each rinse, the tissue is gently agitated and massaged to remove gross blood clots and/or blood components. The used rinse solution is discarded after each rinse. In another embodiment, other portions of the placenta, such as the chorion plate including the amnion, may be retained. In another embodiment, the chorionic sac may be removed and processing the villous chorion with the placenta. In another embodiment, a smaller portion of the placenta may be processed.

After rinsing, the tissue is cleaned and decellularized 30 through submersion in a non-ionic surfactant/detergent solution made with sterile water. The tissue is rinsed in the decellularizing solution, preferably a 0.1% Triton X-100 solution, at a minimum for thirty minutes and a maximum of sixty minutes. Triton X-100 is well known non-ionic mild detergent/surfactant known to decellularize tissue through targeting lipid-lipid and lipid-protein interactions and leaving protein-protein interactions intact. The concentration of 0.1% is preferred as it provides minimal impact to the remainder of the tissue. Other mild detergents may be used such as sodium dodecyl sulfate (SDS) or trypsin. After decellularization is complete, the tissue is rinsed at least one time with 0.9% sterile saline and sterile water for the purposes of further cleaning the tissue, hydrating it, and removing the non-ionic surfactant/detergent. The tissue is then placed in a sterile container.

After decellularization, the tissue is partitioned 40 using a weak organic acid. The excess water from the tissue is removed by gently dabbing the tissue with a lap sponge. The tissue is weighed and placed in a sterile, sealable plastic container. A solution of a weak organic acid is added to the container to submerge the tissue. Generally, a ratio of four ml of the weak organic acid solution per gram of tissue is sufficient to ensure complete submersion of the placental tissue. However, more or less weak organic acid may be added to achieve complete submersion of the placental tissue. The weak organic acid solution has a pH of less than four, but preferably less than two.

The container with the tissue and weak organic acid solution is placed on an orbital shaker and set to a medium speed. The container should shake for a minimum of 180 minutes at ambient temperature. The acidic environment solubilizes the placental ECM macromolecules, partitioning it from the insoluble fraction of the placental tissue. The macromolecules of placental ECM, including collagens (types I, III, V, VI, IX, and X), elastin, laminin, and fibronectin, separate from the insoluble tissue and solubilize in the weak organic acid solution. These components are referred to herein as soluble placental ECM. When the partitioning time is complete, remove the container from the orbital shaker and discard the insoluble tissue. The remaining solution contains the soluble placental ECM.

Citric acid, in a 2M concentration, may be used as the weak organic acid and may be prepared by dissolving approximately 210 grams of citric acid in 500 mL of sterile water. Citric acid is a weak, naturally occurring organic acid, widely used in commercial food products, generally recognized as safe, and can be obtained as anhydrous (water-free) or as monohydrate.

The solubilized placental ECM solution then undergoes prefiltration 50 to remove any remaining gross debris. This step may be accomplished through filling a sterile syringe with the solubilized placental ECM solution and attaching the syringe to a filter such as a PolyCap. The solubilized placental ECM solution is pushed through the filter and collected in a new sterile container. Alternatively, a vacuum hose filtration system may be used. The solubilized placental ECM solution is preferably filtered with a low-protein binding filter having a porosity of 0.45 μm or smaller to prevent any particulate from obstructing the filter. The pH of the solubilized placental ECM solution generally remains less than two and the solution is generally clear without particulate. The total volume of the prefiltered soluble placental ECM is recorded.

Figure 2:
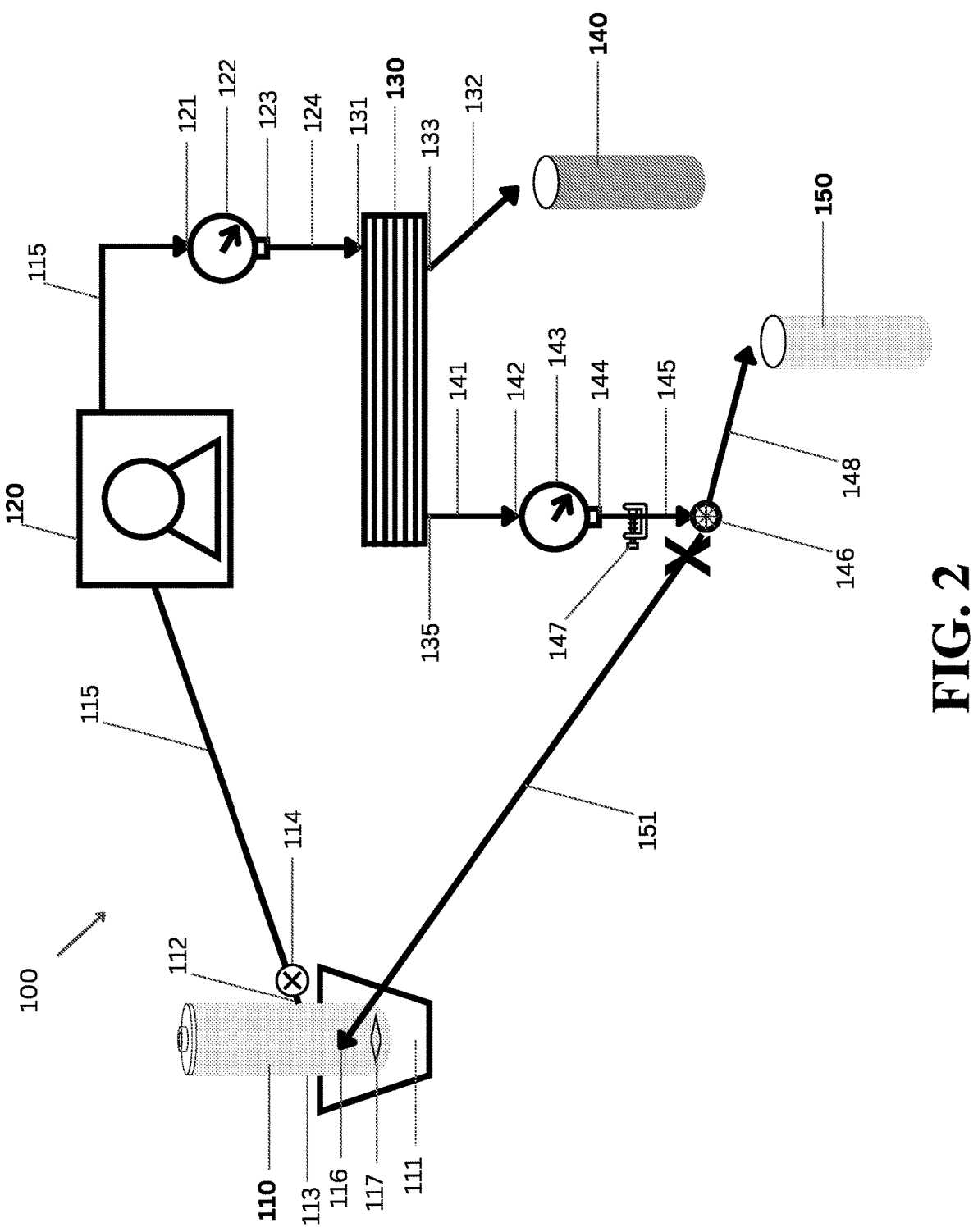
FIG. 2 is a diagram of the tangential flow filtration system during setup.

The ultrafiltration 60 and diafiltration 70 steps are preformed using the tangential flow filtration system 100 identified in FIG. 2. The tangential flow filtration system 100 comprises a receiving reservoir 110, a peristaltic pump 120, a 10,000 Dalton (10 kDa) molecular weight cutoff membrane a low-protein binding membrane filter 130 (e.g., Pall Life Sciences Minimate™ TFF Capsule), filter waste outlet collection reservoir 140, and a tissue outlet collection reservoir 150. The low protein binding membrane filter is preferrable as it reduces the risk of placental ECM binding to it and obstructing the membrane filter.

The receiving reservoir 110 rests on a stir plate 111 with a magnetic stirrer 117 placed within the receiving reservoir 110. The receiving reservoir 110 has an outlet 112 positioned near the bottom of the sidewall 113 that is fluidly connected to a one-way valve 114 that only allows outflow from the receiving reservoir 110. Tubing 115 connects the one-way valve 114 to an inlet 121 of the first pressure gauge 122. Tubing 115 is clamped into the jaws of the peristaltic pump's 120 head. One end of tubing 124 is fluidly connected to an outlet 123 of the first pressure gauge 122 with the other end fluidly connected to an inlet 131 of the membrane filter 130. The membrane filter 30 has a permeate (or filtrate) outlet 133 and a retentate outlet 135. One end of tubing 132 is fluidly connected to the permeate (or filtrate) outlet 133 of the membrane filter 130 with the other end of the tubing 132 emptying into the filter waste outlet collection reservoir 140. One end of tubing 141 is fluidly connected to the retentate outlet 135 with the other end fluidly connected to an inlet 142 of the second pressure gauge 143. One end of tubing 145 is fluidly connected to the outlet 144 of the second pressure gauge 143 with the other end fluidly connected to the inlet of a three-way valve 146. A clamp 147 is located on the tubing 145. Tubing 148 is fluidly connected on one end to the first outlet on the three-way valve 146 with the other end emptying into the tissue outlet collection reservoir 150. One end of the tubing 151 is fluidly connected to the second outlet of the three-way valve 146 with the other end of the tubing 151 fluidly connected to the inlet 116 of the receiving reservoir 110. Tubing is generally connected to each outlet or inlet through a standard luer lock ring and clamp system. All components of the tangential flow filtration system 100 should be sterile or sterilizable to prevent contamination.

To setup, rinse, and prepare the tangential flow filtration system 100, approximately 500 mL of sterile water is added to the receiving reservoir 110. The stir plate is turned on at such a speed that the magnetic stirrer's 117 spinning does not create a vortex in the sterile water. The peristaltic pump 120 is turned on in a clockwise flow direction and the one-way valve 114 is opened. The sterile water flows out of the receiving reservoir, moved by the peristaltic pump's 120 motion, measured by the pressure gauge 122, and into the membrane filter 130. The sterile water flows across the membrane within the membrane filter 130 causing some sterile water to flow out of the permeate (or filtrate) outlet 133 and the remainder out the retentate outlet 135. The sterile water flowing out the permeate (or filtrate) outlet 133 ultimately ends up in the filter waste outlet collection reservoir 140. The remainder of the sterile water flowing out of the retentate outlet 135, passes through the second pressure gauge 143, and enters the three-way valve 146 and proceeds to empty into the flowable tissue outlet collection reservoir 150. Both pressure gauges, 122 and 143, indicate the pressure of the fluid flow. The three-way valve 146 should be oriented such that the sterile water flows through tubing 148 but does not flow through tubing 151. The clamp 147 is tightened on tubing 145 to increase the flow pressure within the membrane filter 130 such that the output of fluid is approximately equal between the permeate (or filtrate) outlet 133 and the retentate outlet 135. The cycle should be run until there is approximately 10 mL of sterile water remaining in the receiving reservoir 110. The sterile water collected in the filter waste outlet collection reservoir 140 and tissue outlet collection reservoir 150 may be discarded.

Figure 3:
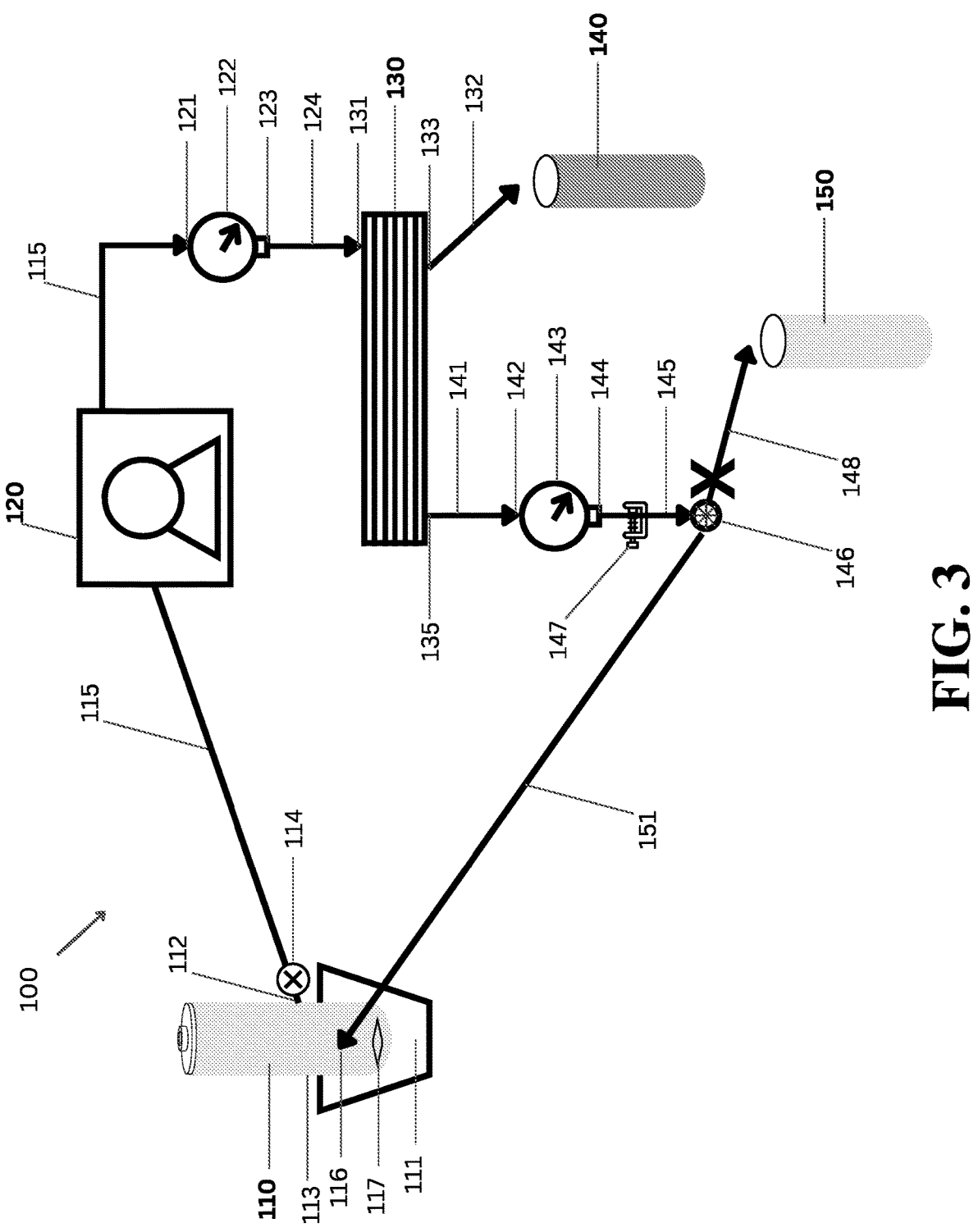
FIG. 3 is a diagram of the tangential flow filtration system during ultrafiltration and diafiltration.

For the ultrafiltration step 60, the tangential flow filtration system 100 is setup according to FIG. 3. The three-way valve 146 is oriented such that the fluid flows through tubing 151 (and into the receiving reservoir 110) but does not flow through tubing 148 (and into the tissue outlet collection reservoir 150). The prefiltered solubilized placental ECM solution is placed into the receiving reservoir 110. The peristaltic pump 120 is turned on, the clamp 147 is tightened on tubing 145 to increase the flow pressure within the membrane filter 130, and the prefiltered solubilized placental ECM solution flows through the tangential flow filtration system 100. When the solubilized placental ECM solution flows into the inlet 131 of the membrane filter 130, the solution flows tangentially across the membrane wherein a portion of the solubilized placental ECM solution, having a size smaller than 10 kDa, flows through the permeate outlet 133, into tubing 132, and empties into the filter waste outlet collection reservoir 140. The remaining prefiltered solubilized placental ECM solution, including the soluble placental ECM, flow through the retentate outlet 135 and ultimately back into the receiving reservoir 110. The soluble placental ECM, such as collagens (types I, III, V, VI, IX, and X), elastin, laminin, and fibronectin, have a molecular weight larger than 10 kDa and cannot pass through the membrane to ultimately empty in the filter waste outlet collection reservoir 140.

The tangential flow filtration system 100 in the configuration, as seen in FIG. 3, is a partially closed loop wherein the portion of the solubilized placental ECM solution, including the soluble placental ECM, that flows through the retentate outlet 135 continues through the tangential flow filtration system 100 until the peristaltic pump 120 is turned off. The pressure gauges should be monitored to ensure the membrane filter 130 does not become obstructed or clogged. As the obstruction increases, the change in pressure differential between pressure gauge 122 and pressure gauge 143 will increase.

The partially closed loop system ultimately reduces the overall starting volume of the receiving reservoir, without reducing the aggregate amount of soluble placental ECM. The ultrafiltration step 60 is performed until the volume of the solubilized placental ECM solution in the receiving reservoir 110 is reduced to a desired volume. For example, the desired volume of 100 mL is preferable as it is a manageable volume in reference to the membrane filter and power of the peristaltic pump. The pH of the ultrafiltered solubilized placental ECM solution generally remains less than two and the solution is generally clear without particulate. The solution in the filter waste outlet collection reservoir 140 is discarded. The desired volume of the ultrafiltered solubilized placental ECM solution is documented.

In some instances, the ultrafiltration step is 60 is unnecessary. If the volume of the prefiltered soluble placental ECM is the same or similar to the desired volume identified above during the ultrafiltration step 60, then ultrafiltration is not necessary and the diafiltration step may be directly performed.

The diafiltration step 70 utilizes a salt-based basic solution and an exchange solution in a ratio of one-part solubilized placental ECM solution and ten parts exchange solution. The salt-based basic solution is added directly to the ultrafiltered solubilized placental ECM solution to effectively and immediately increase the pH from below two. By way of example, if the desired volume of the ultrafiltered solubilized placental ECM solution is 100 mL, then a salt-based basic solution is added directly to the solubilized placental ECM solution in the receiving reservoir 110, and then, 1,000 mL of the exchange solution is added directly in the receiving reservoir 110. The exchange solution also helps increase the pH of the solubilized placental ECM solution. Alternatively, the exchange solution may be added to the receiving reservoir 110 in aliquots as the peristaltic pump 120 operates.

Ultimately, diafiltration results in reducing the molar concentration of the weak organic acid. For 2M citric acid within the ultrafiltered solubilized placental ECM solution, the diafiltration step 80 reduces it to 0.2 M. The peristaltic pump 120 should be turned off when the the volume of the solubilized placental ECM solution reaches the starting volume before the salt-based basic solution and an exchange solution are added. The ratio of 1:10 is a minimum ratio and more exchange solution may be used.

In one embodiment, the salt-based basic solution may be 80 ml of 0.2 M sodium phosphate dibasic in the exchange solution and the exchange solution may be sterile water or a crystalloid solution such as isotonic salts and/or sugar (glucose or dextrose) solutions. Five percent dextrose is preferred as the crystalloid solution as it is readily available, has a pH of approximately 4 (range of 3.5 to 6.2) which further helps reduce the acidity generated by the weak organic acid solution, and has the ideal pH to ensure most, if not all, the placental ECM remains soluble.

In another embodiment, the addition of the salt-based basic solution to the soluble placental ECM may be eliminated and the exchange solution may be used exclusively.

The pH of the solubilized placental ECM solution, after diafiltration, should be between 3.2 to 6.5 with the preferred pH of 4.5. As the pH moves toward neutral, some of the soluble placental ECM becomes insoluble resulting in particulate. The placental ECM particulate may obstruct the membrane filter 130. As such, the ratio of exchange solution to solubilized placental ECM solution, the specific exchange solution, and the use of the salt-based basic solution are important in controlling the pH to reduce the amount of placental ECM particulate. However, the pH is preferred to be above 3.5 so as to reduce the potential of irritation during application to a patient. The choice and concentration of the salt-based basic solution and exchange solution should be guided by the pH parameters to achieve a pH between 3.2 to 6.5 with the preferred pH of 4.5.

Figure 4:
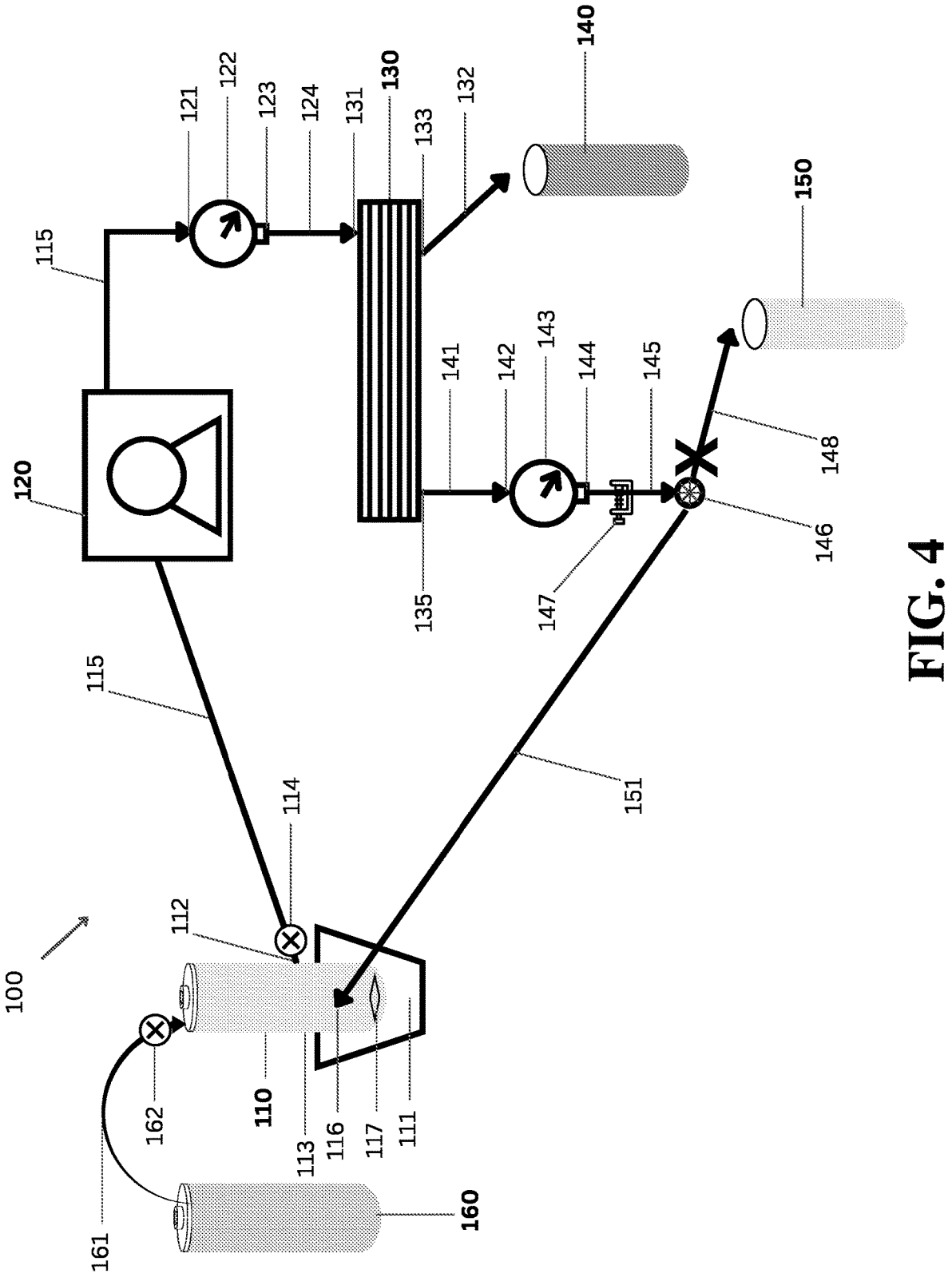
FIG. 4 is a diagram of an alternative tangential flow filtration system used during diafiltration.

FIG. 4 shows a modification to the tangential flow filtration system 100 to perform the diafiltration step 70. In the modified configuration, an exchange solution reservoir 160 is fluidly connected to the receiving reservoir 110 through tubing 161 connected to a one-way valve inlet 162. In this configuration, the receiving reservoir 110 and the exchange solution reservoir 160 are fitted with a pressure cap to maintain the pressure in the reservoir. As the tangential flow filtration system 100 operates, the pressure differential draws exchange solution from the exchange solution reservoir 160, through tubing 161 and into receiving reservoir 110. This modified configuration permits slower addition of the exchange solution to slowly raise the pH of the solubilized placental ECM solution and to potentially avoid or reduce the formation of placental ECM particulate.

Figure 6:
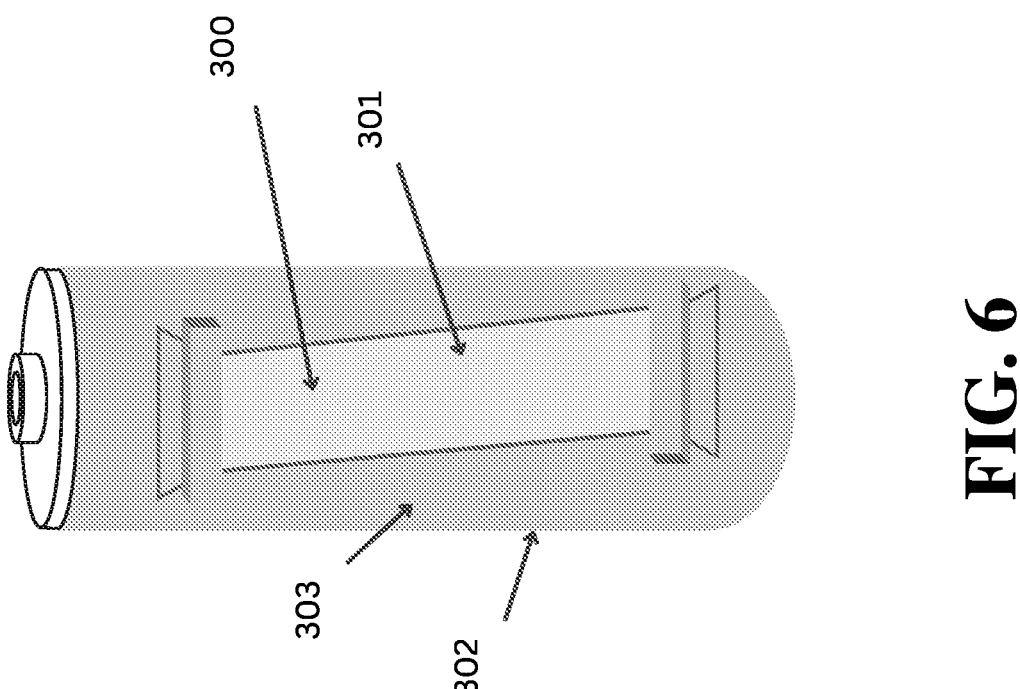
FIG. 6 is a diagram of a dialysis membrane exchange.

As seen in FIG. 6, the diafiltration step 70 may be completed using a dialysis membrane 300 having a molecular weight cutoff of 10 to 40 kDa. The dialysis membrane 300 is filled with the ultrafiltered solubilized placental ECM solution 301. The dialysis membrane 300 is then placed in a sterile container bath 302 filled with the exchange solution 303. In this embodiment the preferred exchange solution is sterile water. The amount of sterile water is approximately a 10:1 ratio to the ultrafiltered solubilized placental ECM solution. The exchange solution should completely cover the dialysis membrane 300. The dialysis membrane should stay submerged in the exchange solution for at least four hours with periodic replacement of the exchange solution. In one embodiment, the exchange solution is changed four times.

After diafiltration, the solubilized placental ECM solution is sterilized 80 according to generally accepted methods including filtration through a 0.2 micron or lower low protein binding filter. Sterilization of the solubilized placental ECM solution is optional and regulatory requirements may specify the exact method of sterilization. Sterilization methods should not alter the characteristics of placental ECM.

The sterilized solubilized placental ECM solution is packaged 90 into small vials. The solubilized placental ECM solution is pipetted into sterile vials with a predetermined amount using a sterile equipment and aseptic technique. Each closed vial shall be placed inside an appropriately sized sterile pouch, sealed, and labeled with a unique allograft ID and documented. The allograft ID should provide sufficient information to identify the donor placenta and the manufacturing processing to include dates, reagents, used, and other notes in accordance with good laboratory practices. In another embodiment, the solubilized placental ECM solution is first packaged 90 then sterilized 80 through exposure to low dose radiation.

A medical provider may use the final solubilized placental ECM solution according to clinical standards and the professional judgment of the physician concerning the patient's care. The final solubilized placental ECM solution should be applied "as needed" meaning the provider should add enough of the final soluble placental ECM product to ensure that the wound surface is covered. The volume necessary will depend on the size of the wound. A covering may then be applied over the wound.

Figure 5:
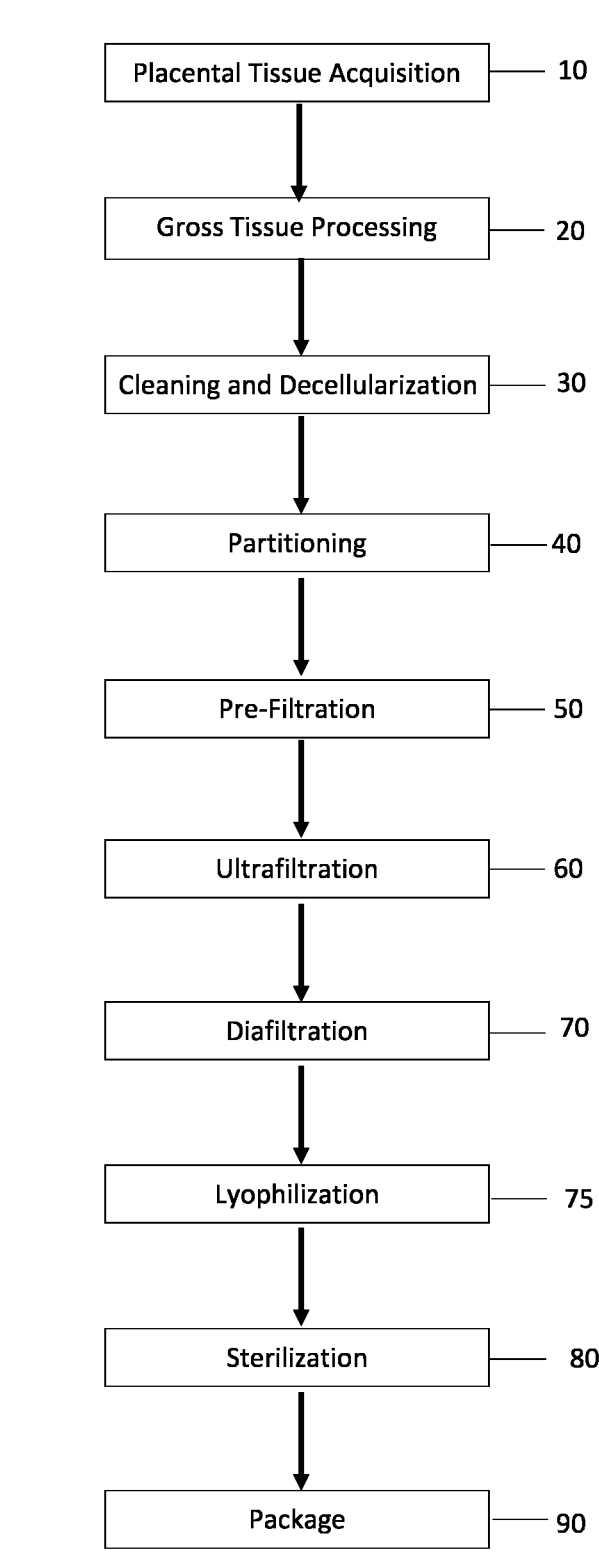
FIG. 5 is an overview flowchart of the manufacturing process for soluble placental ECM for another embodiment.

FIG. 5 depicts an overview of another embodiment of the manufacturing process 200. This embodiment follows the steps of the manufacturing process 1 disclosed herein but further includes a lyophilization step 75 between the diafiltration 70 and sterilization 80. The soluble placental ECM is lyophilized according to standard practice. This freeze-drying process removes virtually all water leaving behind placental ECM particulate. In this embodiment, the preferred exchange solution in the diafiltration step 70 is sterile water so as to not leave behind any sugars or other compounds from the exchange solution in the placental ECM Particulate.

The placental ECM particulate is reconstituted in a storage solution at a ratio of 4 to 1 in volume to weight to achieve a generally liquid final product. The storage solution may be the same as the exchange solution. In one embodiment, the storage solution is five percent dextrose.

Alternatively, the placental ECM particulate may be reconstituted at a lower ratio, such as 1 to 1 in volume to weight, to achieve a higher viscosity resulting in a gel. The components of placental ECM are conducive to generating a spongy, viscous fluid. The concentrations and aggregate amounts of specified placental ECM within the placental ECM particulate are dependent upon the placental ECM concentrations and aggregate amounts in the donor placenta. As a result, the amount of storage solution added to the placental ECM particulate to form the hydrogel varies and may be modified.

The description of the present invention has been presented for purposes of illustration and description and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

We claim:

1. A composition derived from a placental tissue, the composition comprising collagen, elastin, laminin, and fibronectin retained from the placental tissue that are at least partially solubilized in a crystalloid solution having an acidic pH.

2. The composition of claim 1, wherein the acidic pH is from 3.5 to 6.5, inclusive.

3. A method for preparing a solubilized placental extracellular matrix (ECM) composition, the method comprising:
   obtaining at least a portion of a placenta;
   decellularizing the at least portion of the placenta;
   partitioning the at least portion of the placenta in a first solution having a first volume, wherein the first solution comprises an organic acid;
   removing the at least portion of the placenta from the first solution thereby resulting in a second volume of the first solution;

ultrafiltering the second volume of the first solution thereby resulting in a third volume of the first solution; and diafiltrating the third volume of the first solution with an exchange solution to increase the pH thereby resulting in a second solution having a pH of from 3.5 to 6.5, inclusive.

4. The method of claim 3, wherein the partitioning includes submerging the at least portion of the placenta in the first volume of the first solution for at least 180 minutes and agitating the first solution and the at least portion of the placenta.

5. The method of claim 4, wherein the organic acid is citric acid.

6. The method of claim 3, wherein the exchange solution is water, an isotonic salt solution, or a sugar solution.

7. The method of claim 3, wherein the exchange solution is added to the third volume of the first solution in a ratio of 10 to 1.

8. The method of claim 3, further comprising adding a salt-based basic solution to the third volume of the first solution.

9. The method of claim 3, wherein the ultrafiltering is with a 10 kDa tangential flow filter.

10. The method of claim 3, wherein the diafiltrating is with a 10 kDa tangential flow filter.

11. The method of claim 3, further comprising filtering the second volume of the first solution prior to the ultrafiltering.

12. The method of claim 11, wherein the second volume of the first solution is filtered with a 0.45 micron filter.

13. The method of claim 3, further comprising lyophilizing the second solution.

14. The method of claim 13, further comprising reconstituting the lyophilized second solution with dextrose to form a third solution or gel having a higher viscosity than the second solution.

15. A method for preparing a solubilized placental extracellular matrix (ECM) composition, the method comprising:

obtaining at least a portion of a placenta;

decellularizing the at least portion of the placenta;

partitioning the at least portion of the placenta in a first solution having a first volume, wherein the first solution comprises an organic acid;

removing the at least portion of the placenta from the first solution thereby resulting in a second volume of the first solution; and diafiltrating the second volume of the first solution with an exchange solution to increase the pH thereby resulting in a second solution having a pH of from 3.5 to 6.5, inclusive.

16. The method of claim 15, wherein the partitioning includes submerging the at least portion of the placenta in the first volume of the first solution for at least 180 minutes and agitating the first solution and the at least portion of the placenta.

17. The method of claim 15, wherein the exchange solution is water, an isotonic salt solution, or a sugar solution.

18. The method of claim 15, wherein the exchange solution is added to the second volume of the first solution in a ratio of 10 to 1.

19. The method of claim 15, wherein a salt-based basic solution is added to the first solution before the exchange solution.

20. The method of claim 15, wherein the diafiltrating is performed using a 10 kDa tangential flow filter.

21. The composition of claim 1, wherein the crystalloid solution comprises a sugar.

22. The composition of claim 21, wherein the sugar comprises dextrose.

23. The method of claim 15, wherein the diafiltrating is performed using a dialysis membrane.

24. The composition of claim 22, wherein the crystalloid solution comprises five percent dextrose.

\*      \*      \*      \*      \*